(12) United States Patent
Gokhale et al.

(10) Patent No.: US 7,226,932 B2
(45) Date of Patent: Jun. 5, 2007

(54) SELF-EMULSIFYING DRUG DELIVERY SYSTEM

(75) Inventors: Rajeev Gokhale, Vernon Hills, IL (US); Martin J. Griffin, Skokie, IL (US); James E. Truelove, Libertyville, IL (US); James C. Stolzenbach, Buffalo Grove, IL (US); Aziz Karim, Skokie, IL (US); Ajit K. Roy, Glenview, IL (US)

(73) Assignee: G.D. Searle LLC, New York, NY (US)

( * ) Notice: Subject to any disclaimer, the term of this patent is extended or adjusted under 35 U.S.C. 154(b) by 0 days.

(21) Appl. No.: 10/424,998

(22) Filed: Apr. 29, 2003

(65) Prior Publication Data

US 2004/0048934 A1 Mar. 11, 2004

Related U.S. Application Data

(63) Continuation of application No. 08/278,766, filed on Jul. 22, 1994, now abandoned.

(51) Int. Cl.
*A01N 43/42* (2006.01)
*A01N 43/40* (2006.01)

(52) U.S. Cl. .............. 514/311; 514/938; 424/450; 424/455; 546/169

(58) Field of Classification Search ............... 514/311, 514/938; 424/455, 450; 546/169
See application file for complete search history.

(56) References Cited

U.S. PATENT DOCUMENTS

| | | | |
|---|---|---|---|
| 4,388,307 | A | 6/1983 | Cavanak |
| 4,816,247 | A | 3/1989 | Desai et al. |
| 5,206,219 | A | 4/1993 | Desai |
| 5,258,185 | A | 11/1993 | Bauer et al. |
| 5,342,625 | A | 8/1994 | Hauer et al. |
| 5,403,858 | A | 4/1995 | Bastard et al. |
| 5,482,947 | A | 1/1996 | Talley et al. |
| 5,484,801 | A | 1/1996 | Al-Razzak et al. |

FOREIGN PATENT DOCUMENTS

| | | |
|---|---|---|
| EP | 156 507 | 2/1985 |
| EP | 517 412 | 12/1992 |
| JP | 62250941 | 10/1987 |
| WO | WO 92/00750 | 1/1992 |
| WO | WO 95/07696 | 3/1995 |

OTHER PUBLICATIONS

S. H. Yalkowsky, *Drugs and the Pharmaceutical Sciences: Techniques of Solubilization of Drugs*, Marcel Dekker, Inc., vol. 12, 1981, p. 1-224.

Charman et al., Pharm. Res., vol. 9, pp. 87-93, 1992.
Iranloye and Pilpel, J. Pharm. Sci., vol. 73, pp. 1267-1270, 1984.
Wakerly et al., J. Pharm. Pharmacol, vol. 3, suppl., 6P, 1987, p. 242.
Roberts et al., Science, vol. 248, pp. 358-361, 1990.
J.A. Martin, Drugs of the Future, vol. 16(3), pp. 210-212, 1991.
Kagayama et al., Antimicrobial Agents and Chemotherapy, pp. 810-817, 1993.
Lam et al., "De Novo Design and Discovery of Potent, Nonpeptidal HIV-1 Protease Inhibitors", paper 96 at the 205th American Chemical Society National Meeting, Medicinal Chemistry Division, Denver, CO, Mar. 28-Apr. 2, 1993, Abstract Only.
Dorsey et al., "L-735,524: The Rational Design of a Potent and Orally Bioavailable HIV Protease Inhibitor", paper 6 at the 206th American Chemical Society National Meeting, Medicinal Chemistry Division Chicago, IL Aug. 22-27, 1993, Abstract Only.
Wai et al., J. Med. Chem., vol. 36, pp. 249-255, 1993.
Provost et al., Acta Phar. Technol., vol. 35(3), pp. 143-148, 1989.
De Vos et al., J. Pharm. Sciences, vol. 83(5), pp. 641-643, 1994.
Getman et al., J. Med. Chem., "Discovery of a Novel Class of Potent HIV-1 Protease Inhibitors" vol. 36, pp. 288-291, 1993.
Shah et al., Int. Journal of Pharmaceutics, "Self-Emulsifying drug delivery systems (SEODS)" vol. 106, pp. 15-23, 1994.
Mueller et al., Pharm. Research, "Influence of a Fat-Rich Meal on the Pharmaco Kinetics", vol. 11, No. 1, pp. 151-155, 1994.
Hoffman et al., J. Med. Chem, vol. 35, pp. 3784-3791, 1992.
Saari et al., J. Med. Chem., vol. 35, pp. 3792-3802, 1992.
Romero et al., J. Med. Chem. vol. 36, pp. 1505-1508, 1993.
Hargrave, J. Med. Chem., vol. 34, pp. 2231-2241, 1991.
Merluzzi, Science, vol. 250, pp. 1411-1413, 1990.
Williams et al., J. Med. Chem., vol. 36, pp. 1291-1294, 1993.
HSU et al., Proc. Natl. Acad. Sci. USA, vol. 909, pp. 6395-6399, 1993.
Tam et al., "Tat Inhibitors: A New Class Of Anti-HIV Agents" paper 372, at the 204th American Chemical Society National Meeting, Organic Chemistry Division, Washington, DC, Aug. 23-28, 1992, Abstract Only.
Regdon et al., Pharm. Ind., vol. 46, Nr. 11, 1984, No Translation.
Dreyer et al., Biochemistry, "Hydroxyethylene Isostere Inhibitors of HIV-1 Protease", vol. 31, pp. 6646-6659, 1992.
Charman, *Pharmaceutical Research* (New York) 9(1): p. 87-93 (1992).

*Primary Examiner*—Elvis O. Price
(74) *Attorney, Agent, or Firm*—Banner & Witcoff, Ltd.

(57) ABSTRACT

Oral pharmaceutical formulation which improves the bioavailability of pharmaceuticals which are substantially water and oil insoluble is disclosed. In addition to the pharmaceutical, the formulation includes an emulsifier, an oil and an solubilizer. Alternatively, the formulation includes an aqueous solution of solubilizer.

13 Claims, 4 Drawing Sheets

SELF-EMULSIFYING DRUG DELIVERY SYSTEM

CROSS REFERENCE TO RELATED APPLICATIONS

This application is a continuation of application Ser. No. 08/278,766, filed Jul. 22, 1994, now abandoned, which is hereby incorporated by reference in its entirety.

BACKGROUND OF THE INVENTION

The primary targets for any dosage formulation is to deliver the necessary concentration of an active drug to the site of action to elicit the desired therapeutic response and to maintain an effective concentration of the drug for a sufficient period to achieve efficacious treatment. Oral administration is generally preferred but is frequently dependent upon the bioavailability of the active form of the drug, i.e., the rate and extent that the active form of the drug appears from the dosage form in the systemic circulation. Bioavailability is affected by the drug's physical chemical properties, such as pKa, water solubility, oil solubility and stability, as well as its absorption, distribution, metabolism and excretion. It is well known that water insoluble drugs are not generally available for absorption through intestinal lumin and oil insoluble drugs are generally unable to pass across intestine cell membranes into systemic circulation (S. H. Yalkowsky, "DRUGS AND THE PHARMACEUTICAL SCIENCES: TECHNIQUES OF SOLUBILIZATION OF DRUGS," Marcel Dekker, Inc., Vol. 12, 1981). Proper formulation can improve the bioavailability of a drug.

Oral dosage formulations for water soluble or oil soluble drugs are well known. Oral dosage formulations for oil soluble drugs typically require that the oil form an aqueous emulsion. The emulsion may form in the stomach, for example an oil solution in soft gelatin capsules, or be prepared prior to consumption, for example mixing emulsifiable concentrates with an aqueous solution. In both cases, the oil should readily emulsify when released in an aqueous environment. Oils which rapidly emulsify without the use of sophisticated emulsification equipment, such as with gentle shaking or mixing, are known as self-emulsifiable oils. Dosage formulations that utilize such self-emulsifiable oils are known as self-emulsifying drug delivery systems or SEDDS (Charman et al., Pharm. Res. 9:87–93, 1992). Such self-emulsifiable oils are well known and include hydrocarbon oils combined with a surfactant (Iranloye and Pilpel, J. Pharm. Sci. 73:1267–1270, 1984) and vegetable oils combined with a non-ionic surfactant (Wakerly et al., J. Pharm. Pharmacol. 39:suppl. 6p, 1987). More recently, the use of polyglycolyzed glycerides with varying fatty acids and polyethylene glycols chain lengths were used in SEDDS formulations of hydrophobic drugs with adequate oil solubility (Shah et al., Int. J. Pharm. 106:15–23, 1994).

A problem arises when the drug is substantially insoluble in both water and oil. In such cases, the drug is typically poorly bioavailable at best and traditional oral dosage formulations tend not to substantially improve its bioavailability.

BRIEF DESCRIPTION OF THE INVENTION

The present invention is directed to oral dosing formulations of pharmaceuticals which are substantially insoluble in both water and oil. The formulations comprise a pharmaceutical which is substantially water and oil insoluble, an emulsifier, an oil and a solubilizer. Alternatively, the formulation comprises a pharmaceutical which is substantially water and oil insoluble and an aqueous solution of solubilizer.

DETAILED DESCRIPTION OF THE INVENTION

Figure 1:
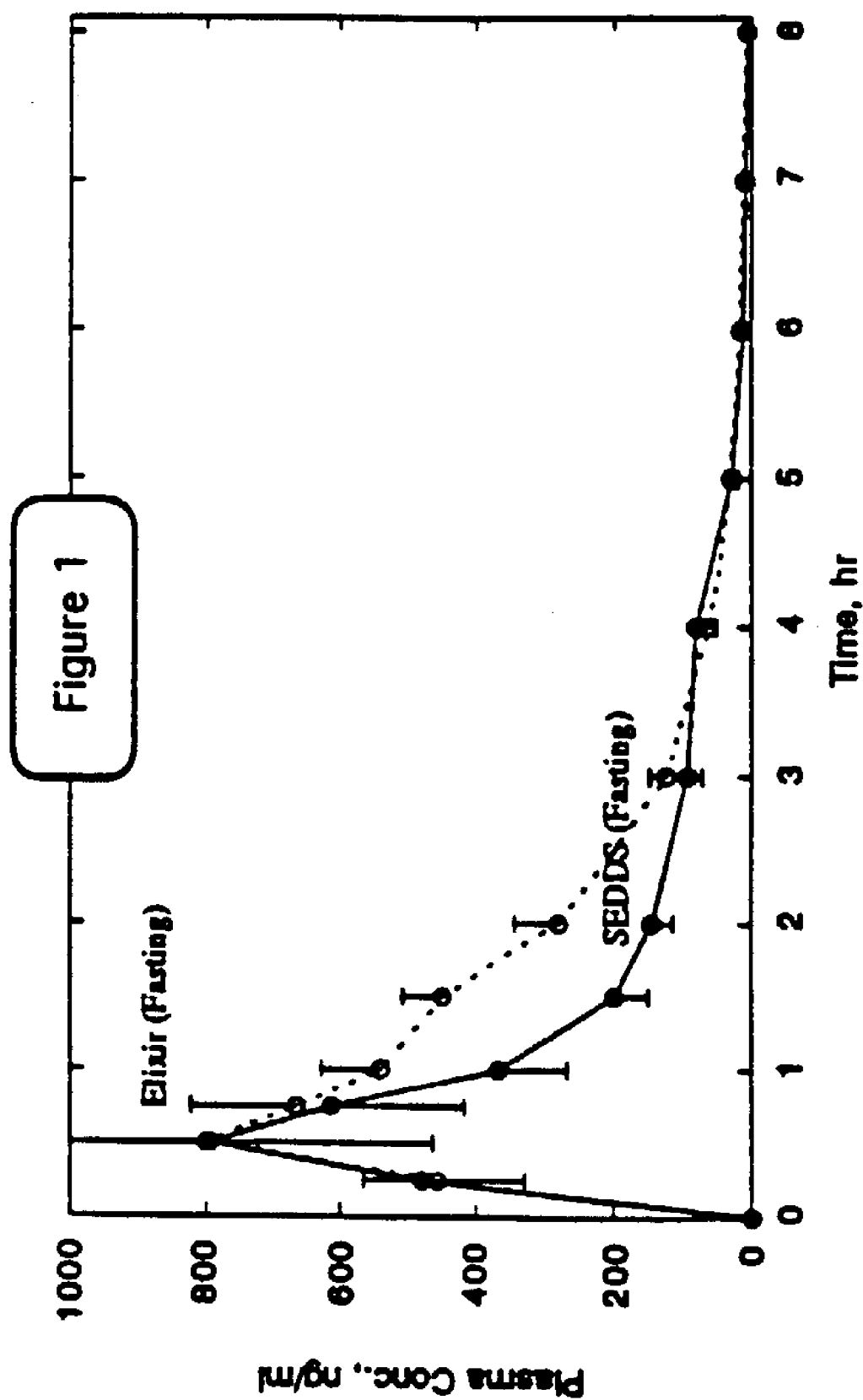
FIG. 1 shows the plasma concentration-time curves of a pharmaceutical with elixir fasting and SEDDS fasting.

The present invention provides a means for orally delivering the necessary concentration of an active form of a pharmaceutical which is substantially insoluble in both water and oil to the systemic circulation of an animal or human being to elicit a desired therapeutic response. Pharmaceuticals, which would otherwise be good candidates for use in treatments, are frequently dropped or rejected due to their substantial insolubility in both water and oil. This insolubility problem typically results in low, if any, bioavailability of the pharmaceutical.

As a class, HIV protease inhibitors tend to have low oral bioavailability and short plasma half-lives. Thus it is difficult to maintain adequate therapeutic blood levels of the drug for a prolonged time period. Surprisingly, by solubilizing the water and oil insoluble pharmaceutical with a solubilizer in the dosage formulation of the present invention, the pharmaceutical's bioavailability substantially increases. For example, the compound $N^1$-[3-[$N^2$-[[(1,1-dimethylethyl)amino]carbonyl]-$N^2$-(2-methylpropyl)amino]-2(R)-hydroxy-1(S)-(phenylmethyl)propyl]-2(S)-[$N^3$-(2-quinolinylcarbonyl)amino]butanediamide which has the formula

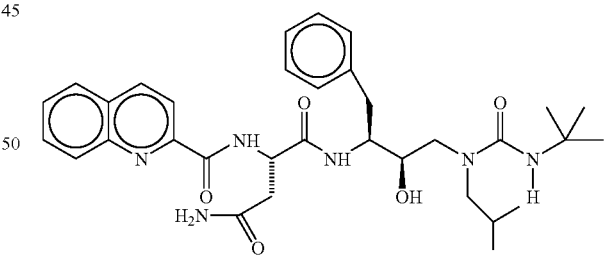

is an effective HIV protease inhibitor (see U.S. patent application Ser. No. 08/152,934, filed Nov. 15, 1993, incorporated herein by reference in its entirety). Because of its low solubility in both water (about 0.01 mg/mL) and oil (less than 1 mg/mL), its bioavailability was also very low when measured in animals. By utilizing a solubilizer in the dosage formulation, the bioavailability increased about 25–30 fold thereby making the compound a potentially effective pharmaceutical for the treatment of HIV infections.

The present invention can also be used with other pharmaceuticals which are not only substantially insoluble in both water and oil, but which are substantially insoluble in water or oil or soluble in water or oil. Such pharmaceuticals include, but are not limited to, Ro 31–8959 (Roberts, N. A. et al. Science 1990, 248, 358–361 and Drugs of the Future 1991, 16(3), 210–212); cyclosporin; FK506 (immunomodulator); [1S-[1R*(R*),2S*]]-2-(acetylamino)-N-[3-[[[(1,1-dimethylethyl)amino]carbonyl](3-methyl-butyl)amino]-2-hydroxy-1-(4-fluorophenylmethyl)propyl]-3,3-dimethyl-butaneamide; [1S-[1R*(2S*,3R*),2S*]]-N1-[3-[[[(1,1-dimethylethyl)amino]carbonyl](3-methylbutyl)amino]-2-hydroxy-1-(phenylmethyl)propyl]-2,3-dimethyl-butanediamide; [1S-[1R*(R*),2S*]]-N-[3-[[[(1,1-dimethylethyl)amino]carbonyl](3-methylbutyl)amino]-2-hydroxy-1-(phenylmethyl)propyl]-2-methyl-3-(2-phenylethylsulfonyl)-propanamide and its diastereomer; [1S-[1R*(S*),2S*]]-3-(4-methoxybenzyl-oxycarbonyl)-N-[3-[[[(1,1-dimethylethyl)amine]carbonyl](3-methylbutyl)amino]-2-hydroxy-1-(phenylmethyl)propyl]-2-methyl-propanamide; [1S-[1R*(R*),2S*]]-N-[3-[[[(1,1-dimethylethyl)amino]carbonyl](3-methylbutyl)amino]-2-hydroxy-1-(phenylmethyl)propyl]-2-methyl-3-(methylsulfonyl)-propanamide and its diastereomer; [2R-hydroxy-3-[N-(4-hydroxyphenylsulfonyl)-N-(2-methyipropyl)amino]-1S-(phenylmethyl)propyl-carbamic acid 3(S)-1,1-dioxotetrahydrothiophen-3-yl-ester; [2R-hydroxy-3-[(4-methoxyphenylsulfonyl)(2-methylpropyl)amino]-1S-(phenylmethyl)propyl-carbamic acid 3(S)-1,1-dioxotetrahydrothiophen-3-yl-ester; N-[2R-hydroxy-3-[[(4-methoxyphenyl)sulfonyl](2-methylpropyl)amino]-1S-(phenylmethyl)propyl]-2,6-dimethylbenzamide; N-[2R-hydroxy-3-[[(4-methoxyphenyl)sulfonyl](2-methylpropyl)amino]-1S-(phenylmethyl)propyl]-2-methyibenzamide; N-[2R-hydroxy-3-[[(4-methoxyphenyl)sulfonyl](2-methylpropyl)amino]-1S-(phenylmethyl)propyl]-2,6-dimethylbenzamide; [1S-[1R*(S*),2S*]]-[3-[[2-hydroxy-3-[(3-methyl-butyl)(phenylsufonyl)amino]-1-(phenylmethyl)propyl] amino]-2-methyl-3-oxopropyl]-carbamic acid (4-methoxyphenyl)methyl ester; N$^1$-[2R-hydroxy-3-[(3-methylbutyl)(phenyl-sulfonyl)amino]-N$^4$-methyl-1S-(phenylmethyl)propyl]-2S-[(2-quinolinylcarbonyl)amino]butanediamide; [1S-[1R*(S*),2S*]]-N$^4$-[2-hydroxy-3-[(3-methylbutyl)(phenylsufonyl)amino]-1-(phenylmethyl)propyl]-2,2,3-trimethyl-butanediamide; [1S-[1R*(R*),2S*]]-N-[2-hydroxy-3-[(3-methylbutyl)](4-aminophenylsufonyl)amino]-1-(phenylmethyl)propyl]-2-methyl-3-(methylsulfonyl)-propanamide; and 8-chlorodibenz[b,f][1,4]oxazapine-10-(11H)-carboxylic acid, 2-[3-(ethylsulfonyl)-l-oxopropyl]hydrazide.

The present invention is particularly beneficial for pharmaceuticals with a dose to solubility ratio in excess of about 1000 and even more beneficial for pharmaceuticals with a dose to solubility ratio in excess of about 10,000. For example, dose to solubility ratio of the compound N$^1$-[3-[N$^2$-[[(1,1-dimethylethyl)amino]carbonyl]-N$^2$-(2-methyipropyl)amino]-2(R)-hydroxy-1(S)-(phenylmethyl)propyl]-2(S)-[N$^3$-(2-quinolinyl carbonyl)amino]butanediamide was determined to be in excess of about 75,000.

The present invention is an oral pharmaceutical composition comprising a) a pharmaceutical which is substantially water and oil insoluble; b) an edible emulsifier; c) an edible oil; and d) an edible solubilizer. The pharmaceutical may be at a concentration within the range of about 0.1 to about 17% (w/w); preferably, at a concentration within the range of about 2 to about 10% (w/w); and more preferably, at a concentration within the range of about 5 to about 10% (w/w). The emulsifier may be at a concentration within the range of about 10 to about 55% (w/w); preferably, at a concentration within the range of about 10 to about 45% (w/w); and more preferably, at a concentration within the range of about 30 to about 45% (w/w). The oil may be at a concentration within the range of about 10 to about 50% (w/w); preferably, at a concentration within the range of about 10 to about 45% (w/w); and more preferably, at a concentration within the range of about 25 to about 45% (w/w). The solubilizer may be at a concentration within the range of about 2 to about 50% (w/w); preferably, at a concentration within the range of about 5 to about 40% (w/w); and more preferably, at a concentration within the range of about 10 to about 35% (w/w).

Alternatively, the present invention is an oral pharmaceutical composition comprising a) a pharmaceutical which is substantially water and oil insoluble; b) an edible solubilizer; and c) water. The pharmaceutical may be at a concentration within the range of about 0.1 to about 17% (w/w), and preferably, at a concentration within the range of about 2 to about 10% (w/w). The solubilizer may be at a concentration in the water within the range of about 40 to about 90% (w/w); preferably, at a concentration within the range of about 50 to about 80% (w/w); and more preferably, at a concentration within the range of about 60 to about 80% (w/w). The solubilizer concentration will frequently depend on the solubility properties of the pharmaceutical and the total volume of the dose.

An "edible emulsifier" is an emulsifier which may be consumed by an animal or human being without substantial side effects or substantial toxic reaction. Emulsifiers which are suitable for use in this invention include polyoxyethylene glycerol esters of fatty acids, such as Tagat TO, Tagat L, Tagat I, Tagat I2 and Tagat O (commercially available from Goldschmidt Chemical Co., Essen, Germany); ethylene glycol esters, such as glycol stearate and distearate; propylene glycol esters, such as propylene glycol myristate; glyceryl esters of fatty acids, such as glyceryl stearates and monostearates; sorbitan esters, such as spans and tweens; polyglyceryl esters, such as polyglyceryl 4-oleate; fatty alcohol ethoxylates, such as Brij type emulsifiers; ethoxylated propoxylated block copolymers, such as poloxamers; polyethylene glycol esters of fatty acids, such as Labrafil 2125 CS, Labrafil M 1944 CS and Labrasol; cremophores, such as cremophore E and Cremophore RH 40P; glycerol monocaprylate/caprate, such as Campmul CM 10; and the like. Tagat TO is preferred.

An "edible oil" is an oil which may be consumed by an animal or human being without substantial side effects or substantial toxic reaction. Most edible oils are suitable for use in this invention, including Neobee oil (commercially available from Stephan Co., Ill.), Myglyol derivatives (fractionated coconut oil), soy oil, almond oil, olive oil, peanut oil, other fatty acid esters of glycerols having about 14 to about 18 carbon atoms, medium chain triglycerides having about 8 to about 10 carbon atoms, and the like. Neobee oil is preferred.

An "edible solubilizer" is a material which can dissolve a pharmaceutical that is substantially insoluble in water and oil and may be consumed by an animal or human being without substantial side effects or substantial toxic reaction. Solubilizers which are suitable for use in this invention include ethanol, tert-butanol, sweet peppermint flavor, orange oil flavor, cherry flavor, raspberry flavor, lemon oil flavor, oleic acid, linoleic acid, propylene glycol, butyric acid, propionic acid, lauryl alcohol, limonene, myristyl alcohol, polyethylene glycol and the like. Ethanol is preferred.

"Substantially water insoluble" means that the measurable solubility in water (pH 7) is preferably less than one part per hundred, more preferably less than one part per thousand and most preferably less than one part per ten thousand.

"Substantially oil insoluble" means that the measurable solubility in oil is preferably less than one part per hundred, more preferably less than one part per thousand and most preferably less than one part per ten thousand.

Typically the formulation of the present invention is prepared by forming an "emulsifiable concentrate" comprising the pharmaceutical, solubilizer, emulsifier and oil in the final concentration ranges disclosed above. The emulsifiable concentrate is preferably prepared by first dissolving the pharmaceutical in the solubilizer. The pharmaceutical is preferably fully dissolved in the solubilizer, which may require vigorous mixing, stirring or heating. This solution is combined with the emulsifier to form a uniform solution. This mixture is then combined with the oil to form the emulsifiable concentrate.

The emulsifiable concentrate may be used directly, for example, as an elixir or in soft gelatin capsules, or may be combined with an aqueous solution prior to distribution or use. Because a preferred emulsifiable concentrate spontaneously forms emulsions in aqueous solutions, it may be combined with the aqueous solution just prior to use which can minimize the effect of any long term emulsion instability. It may be necessary in some formulations to combine the emulsifiable concentrate with the aqueous solution just prior to use to avoid gelling of the mixture. For example, the composition of Tagat TO, Neobee Oil, ethanol and an aqueous solution has been observed to form a gel above five degrees Celsius. The aqueous solution may be water (such as buffered water), beverages (such as soft drinks, milk and the like), juices (such as orange juice, grape juice, apple juice, and the like) and the like. Preferably, the aqueous solution has a pH within the range of about 3 to about 8.5 and more preferably, within the range of about 5 to about 7.5. The preferred ratio of emulsifiable concentrate to aqueous solution, i.e., oil:water ratio, is within the range of about 1:5 to about 1:1000 and more preferably, within the range of about 1:50 to about 1:200.

The particle size of the emulsion particles may be critical to the effectiveness of the present invention. The smaller the emulsion particles, the larger the total surface area and the greater the likelihood of absorption into the systemic circulation. The particle size distribution can be readily determined from dynamic light scattering techniques well known in the art. Preferably the mean emulsion particle size is within the range from about 20 nm to about 25 nm in diameter and more preferably, about 22 nm in diameter.

With regards to the compound $N^1$-[3-[$N^2$-[[(1,1-dimethylethyl)amino]carbonyl]-$N^2$-(2-methylpropyl)amino]-2(R)-hydroxy-1(S)-(phenylmethyl)propyl]-2(S)-[$N^3$-(2-quinolinylcarbonyl)amino]butanediamide, a preferred formulation under the present invention is about 5% (w/w) pharmaceutical, about 35% (w/w) Tagat TO, about 25% (w/w) Neobee Oil and about 35% (w/w) ethanol.

While the pharmaceutical of the present invention may be administered as the sole active pharmaceutical agents, the pharmaceutical may also be used in combination with other pharmaceuticals which are effective for the same treatment. These additional pharmaceuticals may be added to the formulation of present invention and may be water soluble, oil soluble, or substantially water or oil insoluble. For example, $N^1$-[3-[$N^2$-[[(1,1-dimethylethyl)amino]carbonyl]-$N^2$-(2-methylpropyl)amino]-2(R)-hydroxy-1(S)-(phenylmethyl)propyl]-2(S)-[$N^3$-(2-quinolinylcarbonyl)amino]butanediamide may be administered as the sole active pharmaceutical agent, it may also be used in combination with other antiviral agents which are effective against retroviruses such as HIV. Such compounds include, but are not limited to, other HIV protease inhibitors, various nucleoside analogs, nonnucleoside reverse transcriptase inhibitors, tat antagonists and glycosidase inhibitors (U.S. patent application Ser. No. 08/253,638, filed Jun. 3, 1994, which is incorporated by reference herein in its entirety). Such other antiviral agents may also be added to the formulation of the present invention.

Examples of HIV protease inhibitors include, but not limited to, Ro 31–8959 (Roberts, N. A. et al. Science 1990, 248, 358–361 and Drugs of the Future 1991, 16(3), 210–212), KNI-272, (Kagayama, S., et al. Antimicrobial Agents and Chemotherapy 1993, 810–817), the cyclic urea series (Lam, P., et al., "De Novo Design and Discovery of Potent, Nonpeptidal HIV-1 Protease Inhibitors," paper 96 at the 205th American Chemical Society National Meeting, Medicinal Chemistry Division, Denver, Colo., Mar. 28–Apr. 2, 1993), L-735,524 (Dorsey, B. D., et al., "L-735,524: The Rational Design of a Potent and Orally Bioavailable HIV Protease Inhibitor," paper 6 at the 206th American Chemical Society National Meeting, Medicinal Chemistry Division, Chicago, Ill., Aug. 22–27, 1993) and analogs thereof.

Examples of competitive nucleoside analogs include, but are not limited to, azidothymidine (AZT), dideoxyinosine (DDI), DDC, 3TC, D4T and PMEA. Examples of non-nucleoside, non-competitive reverse transcriptase inhibitors include, but are not limited to, the pyridone class (Wei, J. S., et al. J. Med. Chem. 1993, 36, 249–255; Hoffman, J. M., et al. J. Med. Chem. 1992, 35, 3784–3791; Saari et al. J. Med. Chem. 1992, 35 3792–3802; Drugs of the Future 1992, 17(4), 283–285, and analogs thereof); the bis-(heteroaryl) piperazines class (Romero, D. L., et al. J. Med. Chem. 1993, 36, 1505–1508; Romero, D. L., et al. Proc. Natl. Acad. Sci. USA 1991, 34, 746–751 and 3187–3198; and analogs thereof) and the tricyclic pyridobenzo- and depyridodiazepinones (Hargrave, K. D., J. Med. Chem. 1991, 34, 2231–2241; Merluzzi, M. J. Science 1990, 250, 1411–1413; and analogs thereof) and 5-chloro-3-(phenylsulfonyl)indole-2-carboxamide and its analogs (Williams, T. M. et al., J. Med. Chem. 1993, 36, 1291–1294). Examples of tat antagonists include, but are not limited to, Ro 5–3335 and Ro 24–7429 (Hsu, M. C. et al., Proc. Natl. Acad. Sci. USA 1993, 909, 6395–6399; Tam, S. et al., "TAT INHIBITORS: A NEW CLASS OF ANTI-HIV AGENTS," paper 372, at the 204th American Chemical Society National Meeting, Organic Chemistry Division, Washington, D.C., Aug. 23–28, 1992) and analogs thereof. Examples of glycosidase inhibitors include, but are not limited to, castanospermine, castanospermine 6-butryl ester, N-butyl-1-deoxynojirimycin, N-butyl-1-deoxynojirimycin per-butyl ester and analogs and prodrugs thereof.

Other pharmacologically active or inactive compounds, excipients or additives may be added to the formulation to enhance the efficacy of the pharmaceutical, to reduce the side effects and/or toxic effects of the pharmaceutical, to prolong the duration of the active form of the pharmaceutical in the systemic circulation and the like. Additional ingredients may also be added to the formulation which enhance the stability of the pharmaceutical or formulation, such as anti-oxidants (BHA, BHT, vitamin E, ascorbyl palmitate and the like). Still other ingredients may be added to the formulation, such as colorings, flavorings (sweet peppermint flavor, orange oil flavor, cherry flavor, raspberry flavor, lemon oil flavor and the like), sweeteners (aspartame, saccharin, glucose, sucrose, dextrose and the like) and the like to enhance the receptivity and compliance by patients or other users of the formulations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Preparation of [1S-[1R*(R*),2S*]]-N$^1$[3-[[[(1,1-dimethylethyl)amino]carbonyl](2-methylpropyl) amino]-2-hydroxy-1-(phenylmethyl)propyl]-2-(2-quinolinylcarbonyl)amino]-butanediamide Part A:
To a solution of 75.0 g (0.226 mol) of N-benzyloxycarbonyl-L-phenylalanine chloromethyl ketone in a mixture of 807 mL of methanol and 807 mL of tetrahydrofuran at −2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1L). The solution was washed sequentially with 1M potassium hydrogen sulfate, saturated sodium bicarbonate and then saturated sodium chloride solutions. After drying over anhydrous magnesium sulfate and filtering, the solution was removed under reduced pressure. To the resulting oil was added hexane (approx. 1L) and the mixture warmed to 60° C. with swirling. After cooling to room temperature, the solids were collected and washed with 2L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150–151° C. and M+Li$^+$=340.

Part B:
To a solution of 6.52 g (0.116 mol, 1.2 equiv.) of potassium hydroxide in 968 mL of absolute ethanol at room temperature, was added 32.3 g (0.097 mol) of N—CBZ-3 (S)-amino-1-chloro-4-phenyl-2(S)-butanol. After stirring for fifteen minutes, the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl-3(S)-amino-1,2(S)-epoxy-4-phenylbutane, mp 102–103° C. and MH$^+$298.

Part C:
A solution of N-benzyloxycarbonyl 3(S)-amino-1,2-(S)-epoxy-4-phenylbutane (1.00 g, 3.36 mmol) and isobutylamine (4.90 g, 67.2 mmol, 20 equiv.) in 10 mL of isopropyl alcohol was heated to reflux for 1.5 hours. The solution was cooled to room temperature, concentrated in vacuo and then poured into 100 mL of stirring hexane whereupon the product crystallized from solution. The product was isolated by filtration and air dried to give 1.18 g, 95% of N=[[3(S)-phenylmethylcarbamoyl)amino-2(R)-hydroxy-4-phenylbutyl]N-[(2-methylpropyl)]amine mp 108.0–109.5° C., MH$^+$m/z=371.

Part D:
A solution of [2(R), 3(S)]-N-[[3-(phenylmethylcarbamoyl)amino]-2-hydroxy-4-phenylbutyl]N-[(2-methylpropyl)] amine in 10 ml of tetrahydrofuran was treated with tert-butylisocyanate (267 mg, 2.70 mmol) at room temperature for 5 minutes. The solvent was removed in vacuo and replaced with ethyl acetate. The ethyl acetate solution was washed with 5% citric acid, water, and brine, dried over anhydrous MgSO$_4$, filtered and concentrated in vacuo to give 1.19 g, 97% of [2(R),3(S)]-N-[[3-(phenylmethylcarbamoyl)-amino]-2-hydroxy-4-phenyl]-1-[(2-methylpropyl)] amino-2-(1,1-dimethyl)amino]carbonyl]butane, MH$^+$m/z=470.

Part E:
A solution of (1.00 g, 2.21 mmol) [2(R),3(S)]-N-[[3-(phenylmethylcarbamoyl)amino]-2-hydroxy-4-phenyl]-1-[(2-methylpropyl)]amino-1-(1,1-dimethylethyl)amino]carbonyl]butane in 20 mL of methanol was hydrogenated over 10% palladium-on-carbon for 4 hours to give [2(R),3(S)]-N-[[3-amino]-2-hydroxy-4-phenyl]-1-[(2-methylpropyl) amino-1-(1,1-dimethylethyl)amino]carbonyl]butane 720 mg, 97%.

Part F:
A solution of N-Cbz-L-asparagine (602 mg, 2.26 mmol) and N-hydroxybenzotriazole (493 mg, 3.22 mmol) in 2 mL of dimethylformamide was cooled to 0° C. and treated with EDC (473 mg, 2.47 mmol). The solution was allowed to stir at 0° C. for 20 minutes and then treated with [2(R), 3(S)]-N-[[3-amino]-2-hydroxy-4-phenyl]-1-[(2-methylpropyl) lamino-1-(1,1-dimethylethyl)amino]carbonyl]butane (720 mg, 2.15 mmol) in 1 mL of dimethylformamide. The solution was allowed to warm to room temperature and held at this temperature for 7 hours. The reaction mixture was then poured into 100 mL of 60% saturated aqueous sodium bicarbonate-whereupon a white precipitate formed that was isolated by filtration. The filter cake was washed with water, 5% aqueous citric acid, water and then dried in vacuo to give 1.04 g, 83% of [1S-[1R*(R*),2S*]]- N$^1$[3-[[[(1,1-dimethyl-ethyl)amino]-carbonyl](2-methylpropyl)amino]-2-hydroxy-1-(phenylmethyl)propyl]-2-[(phenylmethylcarbamoyl) amino]-butanediamide, mp. 164.0–166.5° C., MH$^+$m/z=584.

Part G:
A solution of [1S-[1R*(R*),2S*]]-N$^1$[3-[[[(1,1-dimethyl-ethyl)amino]carbonyl](2-methylpropyl)amino]-2-hydroxy-1-(phenylmethyl)propyl]-2-[(phenylmethylcarbamoyl)-amino]-butanediamide (1.00 g, 1.72 mmol) in 10 mL of methanol was hydrogenated over 10% palladium-on-carbon for 4 hours to give [1S-[1R*(R*),2S*]]-N$^1$[3-[[[(1,1-dim-ethylethyl)amino]-carbonyl](2-methylpropyl)amino]-2-hydroxy-1-(phenylmethyl)propyl]-2-amino]-butanediamide, 784 mg, 99%.

Part H:
A mixture of [1S-[1R*(R*),2S*]]-N$^1$[3-[[[(1,1-dimethyl-ethyl)amino]carbonyl](2-methylpropyl)amino]-2-hydroxy-1-(phenylmethyl)propyl]-2-amino]-butanediamide, (784 mg, 1.70 mmol), 2-quinoline carboxylic acid N-hydroxysuccinimide ester (459 mg, 1.70 mmol), N-methylmorpholine (343 mg, 3.40 mmol) in 5 mL of dichloromethane was stirred at room temperature for 15 minutes. The solvent was removed in vacuo and replaced with ethyl acetate and the solution washed with 5% aqueous citric acid, saturated aqueous sodium bicarbonate, brine, dried over anhydrous MgSO$_4$, filtered and concentrated in vacuo. The crude product was recrystallized from acetone/hexane to give 790 mg, 77% of [1S-[1R*(R*),2S*]]-N$^1$[3-[[[(1,1-dimethylethyl)amino]carbonyl](2-methyl-propyl)amino]-2-hydroxy-1-(phenylmethyl)propyl]-2-[(2-quinolinylcarbonyl)amino]-butanediamide, mp 107.0–109.8° C., MH$^+$=605.

EXAMPLE 2

Alternative oreparations of the compound from Example 1, Part E: N-[3S-Amino-2R-hydroxy-4-phenylbutyl]-N'-(1,1-dimethylethyl)-N-(2-methyl-propyl)urea Part A: β-2-[Bis(phenylmethyl)amino]benzenepropanol Method 1:

Step 1: A solution of L-phenylalanine (50.0 g, 0.302 mol), sodium hydroxide (24.2 g, 0.605 mol) and potassium carbonate (83.6 g, 0.605 mol) in water (500 mL) was heated to 97° C. Benzyl bromide (108.5 mL, 0.605 mol) was then slowly added (addition time—25 min). The mixture was stirred at 97° C. for 30 minutes under a nitrogen atmosphere. The solution was cooled to room temperature and extracted with toluene (2×250 mL). The combined organic layers were washed with water and brine, dried over magnesium sulfate, filtered and concentrated to an oil. The identity of the product was confirmed as follows. Analytical TLC (10% ethyl acetate/hexane, silica gel) showed major component at Rf value=0.32 to be the desired tribenzylated compound, N,N-bis(phenylmethyl)-L-phenylalanine phenylmethyl ester. This compound can be purified by column chromatography (silica gel, 15% ethyl acetate/hexanes). Usually the product is pure enough to be used directly in the next step without further purification. $^1$H NMR spectrum was in agreement with published literature. EIMS: m/z 434 (M-1).

Step 2: The benzylated phenylalanine phenylmethyl ester (0.302 mol) from the previous reaction was dissolved in toluene (750 mL) and cooled to −55° C. A 1.5 M solution of DIBAL in toluene (443.9 mL, 0.666 mol) was added at a rate to maintain the temperature between −55 to −50° C. (addition time—1 hr). The mixture was stirred for 20 minutes under a nitrogen atmosphere and then quenched at −55° C. by the slow addition of methanol (37 ml). The cold solution was then poured into cold (5° C.) 1.5 N HCl solution (1.8 L). The precipitated solid (approx. 138 g) was filtered off and washed with toluene. The solid material was suspended in a mixture of toluene (400 mL) and water (100 ml). The mixture was cooled to 5° C. and treated with 2.5 N NaOH (186 mL) and then stirred at room temperature until solid dissolved. The toluene layer was separated from the aqueous phase and washed with water and brine, dried over magnesium sulfate, filtered and concentrated to a volume of 75 mL (89 g). Ethyl acetate (25 mL) and hexane (25 mL) were added to the residue upon which the desired alcohol product began to crystallize. After 30 min, an additional 50 mL hexane were added to promote further crystallization. The solid was filtered off and washed with 50 mL hexane to give 34.9 g of first crop product. A second crop of product (5.6 g) was isolated by refiltering the mother liquor. The two crops were combined and recrystallized from ethyl acetate (20 mL) and hexane (30 mL) to give 40 g of ES-2-[Bis(phenyl-methyl)amino]benzenepropanol, 40% yield from L-phenylalanine. An additional 7 g (7%) of product can be obtained from recrystallyzation of the concentrated mother liquor. TLC of product Rf=0.23 (10% ethyl acetate/hexane, silica gel); $[a]_D 25$=+42.4 (c 1.45, $CH_2Cl_2$); DSC 77.67° C.; Anal. Calcd. for $C_{23}H_{25}ON$: C, 83.34; H, 7.60; N, 4.23. Found: C, 83.43; H, 7.59; N, 4.22. HPLC on chiral stationary phase: Cyclobond I SP column (250×4.6 mm I.D.), mobile phase: methanol/triethyl ammonium acetate buffer pH 4.2 (58:42, v/v), flow-rate of 0.5 ml/min, detection with detector at 230 nm and a temperature of 0° C. Retention time: 11.25 min., retention time of the desired product enantiomer: 12.5 min.

Method 2:

L-phenylalaninol (176.6 g, 1.168 mol) was added to a stirred solution of potassium carbonate (484.6 g, 3.506 mol) in 710 mL of water. The mixture was heated to 65° C. under a nitrogen atmosphere. A solution of benzyl bromide (400 g, 2.339 mol) in 3A ethanol (305 mL) was added at a rate that maintained the temperature between 60–68° C. The biphasic solution was stirred at 65° C. for 55 min and then allowed to cool to 10° C. with vigorous stirring. The oily product solidified into small granules. The product was diluted with 2.0 L of tap water and stirred for 5 minutes to dissolve the inorganic by products. The product was isolated by filtration under reduced pressure and washed with water until the pH is 7. The crude product obtained was air dried overnight to give a semi-dry solid (407 g) which was recrystallized from 1.1 L of ethyl acetate/heptane (1:10 by volume). The product was isolated by filtration (at −8° C.), washed with 1.6 L of cold (−10° C.) ethyl acetate/heptane (1:10 by volume) and air-dried to give 339 g (88% yield) of βS-2-[BiS (phenyl-methyl)amino]benzene-propanol, mp 71.5–73.0° C. More product can be obtained from the mother liquor if necessary. The other analytical characterization was identical to compound prepared as described in Part A, Method 1.

Part B: aS-[Bis(phenylmethyl)amino]benzenepropanaldehyde

Method 1:

βS-2-[Bis(phenylmethyl)amino]benzene-propanol (200 g, 0.604 mol) was dissolved in triethylamine (300 mL, 2.15 mol). The mixture was cooled to 12° C. and a solution of sulfur trioxide/pyridine complex (380 g, 2.39 mol) in DMSO (1.6 L) was added at a rate to maintain the temperature between 8–17° C. (addition time—1.0 h). The solution was stirred at ambient temperature under a nitrogen atmosphere for 1.5 hour at which time the reaction was complete by TLC analysis (33% ethyl acetate/hexane, silica gel). The reaction mixture was cooled with ice water and quenced with 1.6 L of cold water (10–15° C.) over 45 minutes. The resultant solution was extracted with ethyl acetate (2.0 L), washed with 5% citric acid (2.0 L), and brine (2.2 L), dried over $MgSO_4$ (280 g) and filtered. The solvent was removed on a rotary evaporator at 35–40° C. and then dried under vaccuum to give 198.8 g of aS-[Bis-(phenylmethyl)amino]-benzenepropanaldehyde as a pale yellow oil (99.9%). The crude product obtained was pure enough to be used directly in the next step without purification. The analytical data of the compound were consistent with the published literature. $[a]_D 25$=−92.9° (c 1.87, $CH_2Cl_2$); HRMS calcd for (M+1) $C_{23}H_{24}NO$ 330.450, found: 330.1836. Anal. Calcd. for $C_{23}H_{23}NO$: C, 83.86; H, 7.04; N, 4.25. Found: C, 83.64; H, 7.42; N, 4.19. HPLC on chiral stationary phase:(S,S) Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of the desired S-isomer: 8.75 min., retention time of the R-enantiomer 10.62 min.

Method 2:

A solution of oxalyl chloride (8.4 ml, 0.096 mol) in dichloromethane (240 ml) was cooled to −74° C. A solution of DMSO (12.0 ml, 0.155 mol) in dichloromethane (50 ml) was then slowly added at a rate to maintain the temperature at −74° C. (addition time about 1.25 hr). The mixture was stirred for 5 min. followed by addition of a solution of βS-2-[bis(phenylmethyl)amino]benzene-propanol (0.074 mol) in 100 ml of dichloromethane (addition time ~20 min., temp. −75° C. to −68° C.). The solution was stirred at −78° C. for 35 minutes under a nitrogen atmosphere. Triethylamine (41.2 ml, 0.295 mol) was then added over 10 min. (temp. −78° to −68° C.) upon which the ammonium salt precipitated. The cold mixture was stirred for 30 min. and then water (225 ml) was added. The dichloromethane layer was separated from the aqueous phase and washed with water, brine, dried over magnesium sulfate, filtered and concentrated. The residue was diluted with ethyl acetate and hexane and then filtered to further remove the ammonium salt. The filtrate was concentrated to give aS-[bis(phenylmethyl)amino]benzenepropanaldehyde. The aldehyde was carried on to the next step without purification.

Method 3:

To a mixture of 1.0 g (3.0 mmoles) of β-2-[bis(phenylmethyl)amino]benzenepropanol 0.531 g (4.53 mmoles) of N-methyl morpholine, 2.27 g of molecular sieves (4A) and 9.1 mL of acetonitrile was added 53 mg (0.15 mmoles) of tetrapropylammonium perruthenate (TPAP). The mixture was stirred for 40 minutes at room temperature and concentrated under reduced pressure. The residue was suspended in 15 mL of ethyl acetate, filtered through a pad of silica gel. The filtrate was concentrated under reduced pressure to give a product containing approximately 50% of aS-2-[bis(phenylmethyl)amino]benzene propanaldehyde as a pale yellow oil.

Method 4:

To a solution of 1.0 g (3.02 mmoles) of βS-2-[bis(phenylmethyl)amino]benzenepropanol in 9.0 mL of toluene was added 4.69 mg (0.03 mmoles) of 2,2,6,6-tetramethyl-1-piperidinyloxy, free radical (TEMPO), 0.32 g (3.11 mmoles) of sodium bromide, 9.0 mL of ethyl acetate and 1.5 mL of water. The mixture was cooled to 0° C. and an aqueous solution of 2.87 mL of 5% household bleach containing 0.735 g (8.75 mmoles) of sodium bicarbonate and 8.53 mL of water was added slowly over 25 minutes. The mixture was stirred at 0° C. for 60 minutes. Two more additions (1.44 mL each) of bleach was added followed by stirring for 10 minutes. The two phase mixture was allowed to separate. The aqueous layer was extracted twice with 20 mL of ethyl acetate. The combined organic layer was washed with 4.0 mL of a solution containing 25 mg of potassium iodide and water (4.0 mL), 20 mL of 10% aqueous sodium thiosulfate solution and then brine solution. The organic solution was dried over magnesium sulfate, filtered and concentrated under reduced pressure to give 1.34 g of crude oil containing a small amount of the desired product aldehyde, aS-[bis(phenylmethyl)amino]benzenepropanaldehyde.

Method 5:

Following the same procedures as described in Part B, Method 1 except 3.0 equivalents of sulfur trioxide pyridine complex was used and aS-[bis(phenylmethyl)amino]benzenepropanaldehyde was isolated in comparable yields.

Part C: N,N,aS-Tris(phenylmethyl)-2S-oxiranemethanamine

Method 1:

A solution of aS-[Bis(phenylmethyl)amino]benzene-propanaldehyde (191.7 g, 0.58 mol) and chloroiodomethane (56.4 mL, 0.77 mol) in tetrahydrofuran (1.8 L) was cooled to −30 to −35° C. (colder temperature such as −70° C. also worked well but warmer temperatures are more readily achieved in large scale operations) in a stainless steel-reactor under a nitrogen atmosphere. A solution of n-butyllithium in hexane (1.6 M, 365 mL, 0.58 mol) was then added at a rate that maintained the temperature below −25° C. After addition the mixture was stirred at −30 to −35° C. for 10 minutes. More additions of reagents were carried out in the following manner: (1) additional chloroiodomethane (17 mL) was added, followed by n-butyllithium (110 mL) at <−25° C. After addition the mixture was stirred at −30 to −35° C. for. 10 minutes. This was repeated once. (2) Additional chloroiodomethane (8.5 mL, 0.11 mol) was added, followed by n-butyllithium (55 mL, 0.088 mol) at <−25° C. After addition the mixture was stirred at −30 to −35° C. for 10 minutes. This was repeated 5 times. (3) Additional chloroiodomethane (8.5 mL, 0.11 mol) was added, followed by n-butyllithium (37 mL, 0.059 mol) at <−25° C. After addition the mixture was stirred at −30 to −35° C. for 10 minutes. This was repeated once. The external cooling was stopped and the mixture warmed to ambient temp over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material. (The crude product weight was >100%. Due to the relative instability of the product on silica gel, the crude product is usually used directly in the next step without purification). The diastereomeric ratio of the crude mixture was determined by proton NMR: (2S)/(2R): 86:14. The minor and major epoxide diastereomers were characterized in this mixture by tlc analysis (silica gel, 10% ethyl acetate/hexane), Rf=0.29 & 0.32, respectively. An analytical sample of each of the diastereomers was obtained by purification on silica-gel chromatography (3% ethyl acetate/hexane) and characterized as follows: N,N,aS-Tris(phenylmethyl)-2S-oxiranemethanamine, HRMS calcd for $C_{24}H_{26}NO$ (M+1) 344.477, found 344.2003; and N,N,aS-Tris(phenylmethyl)-2R-oxiranemethanamine, HPLC on chiral stationary phase: Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of (8): 9.38 min., retention time of enanatiomer of (4): 13.75 min.

Method 2:

A solution of the crude aldehyde 0.074 mol and chloroiodomethane (7.0 ml, 0.096 mol) in tetrahydrofuran (285 ml) was cooled to −78° C., under a nitrogen atmosphere. A 1.6 M solution of n-butyllithium in hexane (25 ml, 0.040 mol) was then added at a rate to maintain the temperature at −75° C. (addition time—15 min.). After the first addition, additional chloroiodomethane (1.6 ml, 0.022 mol) was added again, followed by n-butyllithium (23 ml, 0.037 mol), keeping the temperature at −75° C. The mixture was stirred for 15 min. Each of the reagents, chioroiodomethane (0.70 ml, 0.010 mol) and n-butyllithium (5 ml, 0.008 mol) were added 4 more times over 45 min. at −75° C. The cooling bath was then removed and the solution warmed to 22° C. over 1.5 hr. The mixture was poured into 300 ml of saturated aq. ammonium chloride solution. The tetrahydrofuran layer was separated. The aqueous phase was extracted with ethyl acetate (1×300 ml). The combined organic layers were washed with brine, dried over magnesium sulfate, filtered and concentrated to give a brown oil (27.4 g). The product could be used in the next step without purification. The desired diastereomer can be purified by recrystallization at a subsequent step. The product could also be purified by chromatography.

Method 3:

A solution of aS-[Bis(phenylmethyl)amino]benzene-propanaldehyde (178.84 g, 0.54 mol) and bromochloromethane (46 mL, 0.71 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyllithium in hexane (1.6 M, 340 mL, 0.54 mol) was then added at a rate that maintained the temperature below −25° C. After addition the mixture was stirred at −30 to −35° C. for 10 minutes. More additions of reagents were carried out in the following manner: (1) additional bromochloromethane (14 mL) was added, followed by n-butyllithium (102 mL) at <−25° C. After addition the mixture was stirred at −30 to −35° C. for 10 minutes. This was repeated once. (2) Additional bromochloromethane (7 mL, 0.11 mol) was added, followed by n-butyllithium (51 mL, 0.082 mol) at <−25° C. After addition the mixture was stirred at −30 to −35° C. for 10 minutes. This was repeated 5 times. (3) Additional bromochloromethane (7 mL, 0.11 mol) was added, followed by n-butyllithium (51 mL, 0.082 mol) at <−25° C. After addition the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material.

Method 4:

Following the same procedures as described in Part C, Method 3 except the reaction temperatures were at −20° C. The resulting N,N,aS-tris(phenylmethyl)-2S-oxiranemethanamine was a diastereomeric mixture of lesser purity then that of Method 3.

Method 5:

Following the same procedures as described in Part C, Method 3 except the reaction temperatures were at −70 to −78° C. The resulting N,N,aS-tris(phenylmethyl)-2S-oxiranemethanamine was a diastereomeric mixture, which was used directly in the subsequent steps without purification.

Method 6:

Following the same procedures as described in Part C, Method 3 except a continuous addition of bromochloromethane and n-butyllithium was used at −30 to −35° C. After the reaction and work up procedures as decribed in Method 3, the desired N,N,aS-tris(phenylmethyl)-2S-oxiranemethanamine was isolated in comparable yields and purities.

Method 7:

Following the same procedures as described in Part C, Method 2 except dibromomethane was used instead of chloroiodomethane. After the reaction and work up procedures as decribed in Method 2, the desired N,N,aS-tris (phenylmethyl)-2S-oxirane-methanamine was isolated.

Part D: 3S-[N,N-Bis(phenylmethyl)amino]-1-(2-methylpropyl)amino-4-phenylbutan-2R-ol To a solution of crude N,N,aS,-tris(phenylmethyl)-2S-oxiranemethanamine (388.5 g, 1.13 mol) from Part C in isopropanol (2.7 L) (or ethyl acetate) was added isobutylamine (1.7 kgm, 23.1 mol) over 2 min. The temperature increased from 25° C. to 30° C. The solution was heated to 82° C. and stirred at this temperature for 1.5 h. The warm solution was concentrated under reduced pressure at 65° C. The brown oil residue was transferred to a 3-L flask and dried in vacuo (0.8 mm Hg) for 16 h to give 450 g of 3S-[N,N-bis(phenylmethyl)amino]-1-(2-methylpropyl) amino-4-phenylbutan-2R-ol as a crude oil. The product was used directly in the next step without purification. An analytical sample of the desired major diastereomeric product was obtained by purifying a small sample of crude product by silica gel chromatography (40% ethyl acetate/ hexane). Tlc analysis: silica gel, 40% ethyl acetate/hexane; Rf=0.28; HPLC analysis: ultrasphere ODS column, 25% triethylamine-/phosphate buffer pH 3/acetonitrile, flow rate 1 mL/min, UV detector; retention time 7.49 min.; HRMS calcd for C28H37N2O (M+1) 417.616, found 417.2887. An analytical sample of the minor diastereomeric product, 3S-[N,N-bis(phenylmethyl)amino]-1-(2-methyipropyl)amino-4-phenylbutan-2S-ol was also obtained by purifying a small sample of crude product by silica gel chromatography (40% ethyl acetate/hexane).

Part E: N-[3S-[N,N-Bis(phenylmethyl)amino]-2R-hydroxy-4-phenylbutyl]-N'-(1,1-dimethylethyl)-N-(2-methylpropyl) urea A solution of the crude 3S-[N,N-Bis(phenylmethyl) amino]-1-(2-methylpropyl)amino-4-phenylbutan-2R-ol (446.0 g, 1.1 mol) from Example 4 in tetrahydrofuran (6 L) (or ethyl acetate) was cooled to 8° C. t-Butyl isocyanate (109.5 g, 1.1 mol) was then added to the solution of the amine from an addition funnel at a rate that maintained the temperature between 10–12° C. (addition time was about 10 min). The external cooling was stopped and the reaction was warmed to 18° C. after 30 min. The solution was transferred directly from the reactor to a rotary evaporator flask (10 L) through a teflon tube using vacuum and then concentrated. The flask was heated in a 50° C. water bath during the 2 h required for the distillation of the solvent. The brown residue was dissolved in ethyl acetate (3 L), washed with 5% aq citric acid solution (1×1.2 L), water (2×500 mL), brine (1×400 mL), dried over magnesium sulfate (200 g) and filtered. The volume of product solution was reduced to 671 mL over 2 h on a rotary evaporator at 50° C. The concentrate was stirred and diluted with 1.6 L of hexane. The mixture was cooled to 12° C. and stirred for 15 hours. The product crystals were isolated by filtration, washed with 10% ethyl acetate/hexane (1×500 mL), hexane (1×200 mL) and dried in vacuo (2 mm) at 50° C. for 1 hour to give 248 g of N-[3S-[N,N-bis-(phenylmethyl)amino]-2R-hydroxy-4-phenylbutyl]-N'-(1,1-dimethylethyl)-N-(2-methylpropyl)-urea. The mother liquor and washes were combined and concentrated on a rotary evaporator to give 270 g of a brown oil. This material was dissolved in ethyl acetate (140 mL) at 50° C. and-diluted with hexane (280 mL) and seeded with crystals of the first crop product (20 mg). The mixture was cooled in an ice bath and stirred for 1 h. The solid was isolated by filtration, washed with 10% ethyl acetate/hexane (1×200 mL) and dried in vacuo (2 mm) at 50° C. for 1 h to give 55.7 g of product as the second crop (49% overall yield). Mp 126° C.; [a]D25=−59.0° (c=1.0, CH2Cl2), TLC: Rf 0.31 (silica gel, 25% ethyl acetate/hexane).

Part F: N-[3S-Amino-2R-hydroxy-4-phenylbutyl]-N'-(1,1-dimethylethyl)-N-(2-methylpropyl)urea N-[3S-[N,N-Bis(phenylmethyl)amino]-2R-hydroxy-4-phenylbutyl]-N'-(1,1-dimethylethyl)-N-(2-methylpropyl)urea (125.77 g, 0.244 mol) was dissolved in ethanol (1.5 L) (or methanol) and 20% palladium hydroxide on carbon (18.87 g) (or 4% palladium on carbon) was added to the solution under nitrogen. The mixture was stirred at ambient temperature under a hydrogen atmosphere at 60 psi for approximately 8 h. The catalyst was removed by filtration and the filtrate was concentrated to give 85 g of N-[3S-Amino-2R-hydroxy-4-phenylbutyl]-N'-(1,1-dimethylethyl)-N-(2-methylpropyl)urea as a colorless oil.

Further elaboration on the methods of Example 2 are contained in U.S. patent application Ser. No. 08/156,498, filed Nov. 23, 1993, incorporated herein by reference in its entirety.

EXAMPLE 3

Preparation and Characterizatrion of Emulsifiable Concentrate $N^l$-[3-[$N^2$-[[(1,1-dimethylethyl)amino]carbonyl]-$N^2$-(2-methylpropyl)amino]-2(R)-hydroxy-1(S)-(phenylmethyl)propyl]-2(S)-[$N^3$-(2-quinolinylcarbonyl)amino]butanediamide (0.5 g, 5% w/w) was dissolved in absolute ethanol (3.5 g, 35% w/w) by soaking for fifteen minutes followed by gentle mixing until a clear solution was obtained. To this solution was added Tagat TO (3.5 g, 35% w/w) and the mixture gently mixed to a clear solution. Neobee M5 oil (2.5 g, 25% w/w) was added to the mixture and gently mixed resulting in a clear, slightly viscous solution of the emulsifiable concentrate. The corresponding 2.5% w/w emulsifiable concentrate of the pharmaceutical was also prepared by the same procedure with essentially the same ratio of the other ingredients. The corresponding 15% w/w emulsifiable concentrate of the pharmaceutical was also prepared by the same procedure in 35% w/w ethanol, 40% w/w Tagat TO and 10% w/w Neobee oil. The ethanol concentration of about a 2% w/w emulsifiable concentrate of the pharmaceutical may be reduced to 2% w/w when the Tagat TO concentration is increased to 46% w/w, Neobee oil concentration to 46% w/w and propylene glycol added to a concentration of 4% w/w.

EXAMPLE 4

The emulsifiable concentrate of Example 3 was mixed with water (distilled) at pH 5 or 0.1 N hydrochloric acid (pH 1) to form a turbid solution. At an emulsifiable concentrate:water ratio of 1:50, 1:100 and 1:200, the majority of emulsion particles were measured using dynamic light scattering techniques by laser optics particle sizing (Brookhaven Labs digital collator and Lexal argon ion laser) to be within the range 20 to 25 nm in diameter. The measurement was taken after further diluting an aliquot of the 1:50 ratio mixture to 1:200. The emulsifiable concentrate/water emulsion was stable for at least four hours at 5° C. At an emulsifiable concentrate:water ratio of 1:8, the mixture formed a gel in about ten minutes. Promptly further diluting the 1:8 mixture with 0.1 N hydrochloric acid formed a microemulsion which was stable for at least one hour at ambient temperature. An emulsion of the corresponding 2.5% w/w emulsifiable concentrate of the pharmaceutical from Example 3 was also prepared and found to form microemulsions upon dilution in water.

Tables 1–3 list the typical particle size distributions (PSD) obtained when the emulsifiable concentrate of Example 3 was mixed as described above in a ratio of 1:50 with water (pH 5), 0.1 N hydrochloric acid (pH 1) and the soluble fraction of a partially gelled emulsion in water after standing at 5° C. for one week. The soluble fraction was obtained by centrifuging the mixture in a microcentrifuge for two minutes to produce a clarified solution. The soluble fraction Dilution in water produced a small particle with a peak diameter of 22 nm and a mean diameter of 52 nm which includes a weak contribution from an ill-defined larger diameter mode. Dilution in 0.1 N HCl produced a bimodal particle size distribution with peak diameters of 25 nm and 86 nm and a mean diameter of 61 nm.

TABLE 1

PSD Of Emulsifiable Concentrate In Water 1:50

| d/nm[1] | G (d)[2] | C (d)[3] | d/nm | G (d) | C (d) |
|---|---|---|---|---|---|
| 3 | 0 | 0 | 21 | 100 | 58 |
| 4 | 0 | 0 | 25 | 86 | 83 |
| 5 | 0 | 0 | 29 | 33 | 92 |
| 6 | 0 | 0 | 33 | 9 | 95 |
| 7 | 0 | 0 | 39 | 0 | 95 |
| 9 | 0 | 0 | 45 | 0 | 95 |
| 10 | 0 | 0 | 52 | 0 | 95 |
| 12 | 0 | 0 | 61 | 0 | 95 |
| 13 | 0 | 0 | 70 | 0 | 95 |
| 16 | 22 | 6 | 82 | 0 | 95 |
| 18 | 81 | 29 | 95 | 0 | 95 |
|  |  |  | 110 | 0 | 95 |
|  |  |  | 128 | 0 | 95 |
|  |  |  | 149 | 0 | 95 |
|  |  |  | 173 | 0 | 95 |
|  |  |  | 201 | 0 | 95 |
|  |  |  | 234 | 0 | 95 |
|  |  |  | 272 | 7 | 97 |
|  |  |  | 316 | 6 | 98 |
|  |  |  | 367 | 6 | 100 |
|  |  |  | dust | 0 | 100 |

[1] d/nm = diameter in nanometers of standard
[2] G (d) = differential particle size distribution
[3] C (d) = cumulative particle size distribution

TABLE 2

PSD Of Emulsifiable Concentrate In 0.1 N HCl 1:50

| d/nm[1] | G (d)[2] | C (d)[3] | d/nm | G (d) | C (d) |
|---|---|---|---|---|---|
| 3 | 0 | 0 | 22 | 41 | 33 |
| 4 | 0 | 0 | 25 | 15 | 36 |
| 5 | 0 | 0 | 29 | 0 | 36 |
| 6 | 0 | 0 | 34 | 0 | 36 |
| 7 | 0 | 0 | 40 | 0 | 36 |
| 9 | 0 | 0 | 46 | 16 | 39 |
| 10 | 0 | 0 | 53 | 62 | 58 |

TABLE 2-continued

PSD Of Emulsifiable Concentrate In 0.1 N HCl 1:50

| d/nm[1] | G (d)[2] | C (d)[3] | d/nm | G (d) | C (d) |
|---|---|---|---|---|---|
| 12 | 0 | 0 | 62 | 96 | 68 |
| 14 | 23 | 4 | 72 | 100 | 86 |
| 16 | 51 | 14 | 84 | 56 | 96 |
| 19 | 66 | 26 | 98 | 21 | 100 |
|  |  |  | 114 | 0 | 100 |
|  |  |  | 133 | 0 | 100 |
|  |  |  | 155 | 0 | 100 |
|  |  |  | 180 | 0 | 100 |
|  |  |  | 209 | 0 | 100 |
|  |  |  | 244 | 0 | 100 |
|  |  |  | 284 | 0 | 100 |
|  |  |  | 338 | 0 | 100 |
|  |  |  | 384 | 0 | 100 |
|  |  |  | dust | 0 | 100 |

[1] d/nm = diameter in nanometers of standard
[2] G (d) = differential particle size distribution
[3] C (d) = cumulative particle size distribution

TABLE 3

PSD Of Soluble Fraction Of Partially Gelled Emulsifiable Concentrate (Example 3) In Water 1:50

| d/nm[1] | G (d)[2] | C (d)[3] | d/nm | G (d) | C (d) |
|---|---|---|---|---|---|
| 3 | 0 | 0 | 21 | 53 | 18 |
| 4 | 0 | 0 | 24 | 88 | 42 |
| 5 | 0 | 0 | 28 | 100 | 69 |
| 6 | 0 | 0 | 32 | 62 | 86 |
| 7 | 0 | 0 | 38 | 26 | 93 |
| 9 | 0 | 0 | 44 | 0 | 93 |
| 10 | 0 | 0 | 51 | 0 | 93 |
| 11 | 0 | 0 | 59 | 0 | 93 |
| 13 | 0 | 0 | 68 | 0 | 93 |
| 15 | 0 | 0 | 79 | 0 | 93 |
| 18 | 12 | 3 | 92 | 0 | 93 |
|  |  |  | 107 | 0 | 93 |
|  |  |  | 124 | 0 | 93 |
|  |  |  | 144 | 0 | 93 |
|  |  |  | 167 | 2 | 94 |
|  |  |  | 194 | 3 | 95 |
|  |  |  | 225 | 6 | 96 |
|  |  |  | 261 | 7 | 98 |
|  |  |  | 303 | 5 | 99 |
|  |  |  | 352 | 2 | 100 |
|  |  |  | dust | 0 | 100 |

[1] d/nm = diameter in nanometers of standard
[2] G (d) = differential particle size distribution
[3] C (d) = cumulative particle size distribution

EXAMPLE 5

$N^1$-[3-[$N^2$-[[(1,1-dimethylethyl)amino]carbonyl]-$N^2$-(2-methylpropyl)amino]-2(R)-hydroxy-1(S)-(phenylmethyl)propyl]-2(S)-[$N^3$-(2-quinolinylcarbonyl)amino]butanediamide had a bioavailability of <1% using normal formulation methods apparently due to poor water and oil solubility. When it was administered as a suspension-in tween 80, methylcellulose and water to rats, its bioavailability was about 1%. When crystals of the pharmaceutical were micronized in a Trost Micronizer Apparatus and administered (10 and 100 mg/kg) to dogs in a capsule, no detectable plasma concentration was observed (see Example 7).

EXAMPLE 6

Preparation and Characterizatrion of Elixir $N^1$-[3-[$N^2$-[[(1,1-dimethylethyl)amino]carbonyl]-$N^2$-(2-methylpropyl)amino]-2(R)-hydroxy-1(S)-(phenylmethyl)propyl]-2(S)-[$N^3$-(2-quinolinylcarbonyl)amino]butanediamide (18.75 g) was dissolved in 96% ethanol (117.5 ml) by soaking for ten minutes followed by mixing until a clear solution was obtained. To this solution was added peppermint flavor (15 ml) and the mixture gently mixed to a clear solution. Water (37.5 ml) was added to the mixture and gently mixed resulting in a clear solution of the elixir. The elixir was stored at room temperature protected from light and was not generally used after 21 days.

EXAMPLE 7

Oral Administration to Dogs and Rats

Dogs: $N^1$-[3-[$N^2$-[[(1,1-dimethylethyl)amino]carbonyl]-$N^2$-(2-methylpropyl)amino]-2(R)-hydroxy-1(S)-(phenylmethyl)propyl]-2(S)-[$N^3$-(2-quinolinylcarbonyl)amino]butanediamide was administered in a nonrandomized crossover design to four femal beagle dogs in a series of formulations: (1) elixir (10 mg/kg) (Example 6); (2) a PVP coprecipitate (20 mg/kg) (prepared as follows: polyvinylpyrrolidone (PVP) and the pharmaceutical (ratio of 2.2 w/w) were disolved in ethanol and then the sovent was removed in vacuo; the resulting solids were ground to a fine powder and dosed in capsules); (3) micronized crystals of the pharmaceutical (10 and 100 mg/kg) (Example 5); (4) SEDDS I (20 mg/kg) {emulsifiable concentrate comprising the pharmaceutical (5% w/w), Myglyol (35% w/w), ethanol (15% w/w) and labrafil CS2125 (45% w/w), prepared according to the method of Example 3, was mixed in a ratio of 1:10 with water}; and (5) SEDDS II (20 mg/kg) (emulsifiable concentrate of Example 3 was mixed in a ratio of 1:10 with water). The dogs were given each formulation in the fasted state. The dogs were also given the elixir and SEDDS I formulations with a high fatty meal. After each dose, blood samples were taken from the dogs at 0.25, 0.5, 1, 1.5, 2, 3, 5 and 7 hours. Plasma was obtained by centrifugation and the samples were frozen and stored for analysis.

The pharmaceutical was obtained by solid phase extraction from the plasma and the extracts were analyzed by HPLC. The plasma concentrations of the pharmaceutical were determined and for each dosage form the area under the plasma concentration time curve (AUC), peak plasma concentration ($C_{max}$) and time to reach the peak plasma concentration ($T_{max}$) were calculated. The data is summarized in Table 4.

There were no dectectable concentrations of the pharmaceutical after administration of the micronized form of the pharmaceutical at 10 and 100 mg/kg doses in dogs. The data demonstrate that the pharmaceutical was systemically available after administration of the PVP coprecipitate but the concentrations were very low (under 100 ng/ml). Administration of the alcohol elixir or either of the two SEDDS formulations resulted in higher peak plasma concentrations and AUCs than the coprecipitate. In addition, administering the elixir with food reduced the plasma concentrations of the pharmaceutical as compared to giving the elixir fasted. For the SEDDS vehicle, however, food enhanced the bioavailability of the pharmaceutical.

TABLE 4

Mean Pharmacokinetic Parameters after Oral Administration of Various Dosage Forms to Female Beagle Dogs

| Dosage Form | Dose (mg/kg) | AUC (ng/mL) hr | $C_{max}$ (ng/mL) | $t_{max}$ (hr) |
|---|---|---|---|---|
| Elixir | | | | |
| Fasted | 10.0 | 413. ± 132 | 648. ± 249 | 0.813 ± 0.400 |
| Fed | 10.0 | 148. ± 102 | 222. ± 106 | 0.375 ± 0.072 |
| Emulsion (SEDDS I) | | | | |
| Fasted | 20.0 | 162. ± 93 | 97.5. ± 37.6 | 0.563 ± 0.313 |
| Fed | 20.0 | 319. ± 106 | 213. ± 68 | 0.750 ± 0.421 |
| PVP Coprecipitate | | | | |
| Fasted | 20.0 | 71.0. ± 20.1 | 59.4. ± 10.7 | 1.38 ± 0.55 |
| Emulsion (SEDDS II) | | | | |
| Fasted | 20.0 | 514. ± 111 | 290. ± 52 | 1.44 ± 0.41 |

Rats: $N^1$-[3-[$N^2$-[[(1,1-dimethylethyl)amino]carbonyl]-$N^2$-(2-methylpropyl)amino]-2(R)-hydroxy-1(S)-(phenylmethyl)propyl]-2(S)-[$N^3$-(2-quinolinylcarbonyl)amino]butanediamide was orally administered in vehicles containing polyethylene glycol 400, propylene glycol, ehanol and tween 80 (PPE-tween) or in the SEDDS II formulation. Three rats were administered with each dose vehicle. Plasma samples were obtained at 0.25, 0.5, 1.0, 2.0, 4.0, 6.0 hours after dose administration. Plasma concentrations of the pharmaceutical were determined as previously described in the dog and the same pharmacokinetic parameters were determined. Results are given in Table 5. The data show that in this study the SEDDS II formulation gave the highest plasma concentrations of the pharmaceutical as compared to the PPE-tween vehicle.

TABLE 5

Male Rat Pharmacokinetic Parameters of the Mean Plasma Concentrations after Oral Administration

| Dose Vehicle | Dose (mg/kg) | $AUC^a$ ± $SEM^b$ (μg/mL) hr | $Cmax^c$ ± $SEM^b$ (μg/mL) | $Tmax^d$ ± $SEM^b$ (hr) |
|---|---|---|---|---|
| SEDDS II | 300 | 7.61 ± 2.60 | 1.59 ± 0.50 | 1.58 ± 1.21 |
| 5% Tween | 300 | 0.966 ± 0.400 | 0.422 ± .189 | 0.25 ± 0.0 |
| 10% Tween | 300 | 1.27 ± 0.24 | 0.837 ± 0.228 | 0.333 ± 0.083 |

[a] Area under the plasma concentration-time curve (AUC) measured from 0 through 6.0 hours.
[b] Standard error of the mean.
[c] Peak plasma concentration of the pharmaceutical.
[d] Time to reach the peak plasma concentration.

EXAMPLE 8

Figure 2:
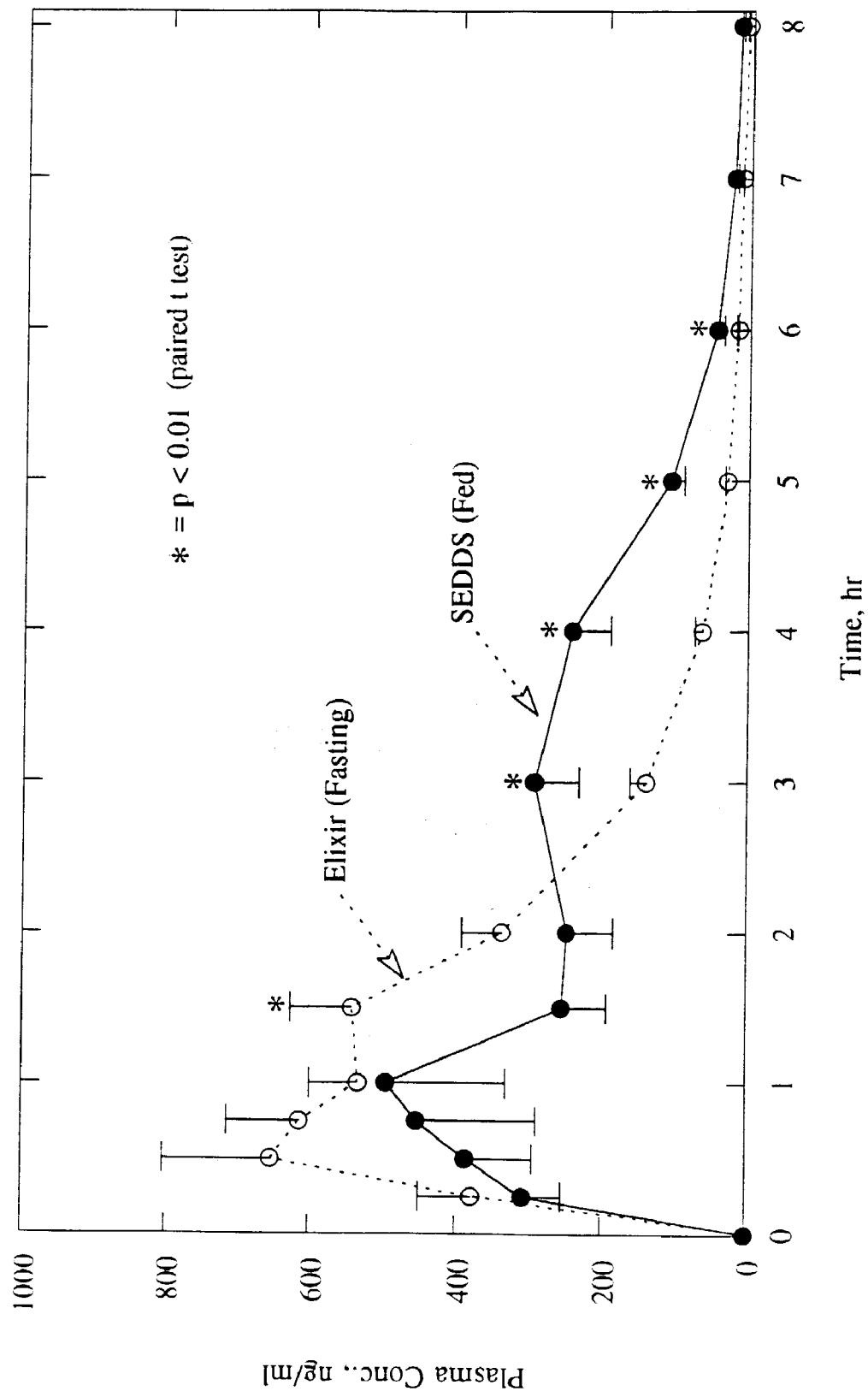
FIG. 2 shows the plasma concentration-time curves of a pharmaceutical with elixir fasting and SEDDS fed.
Figure 3:
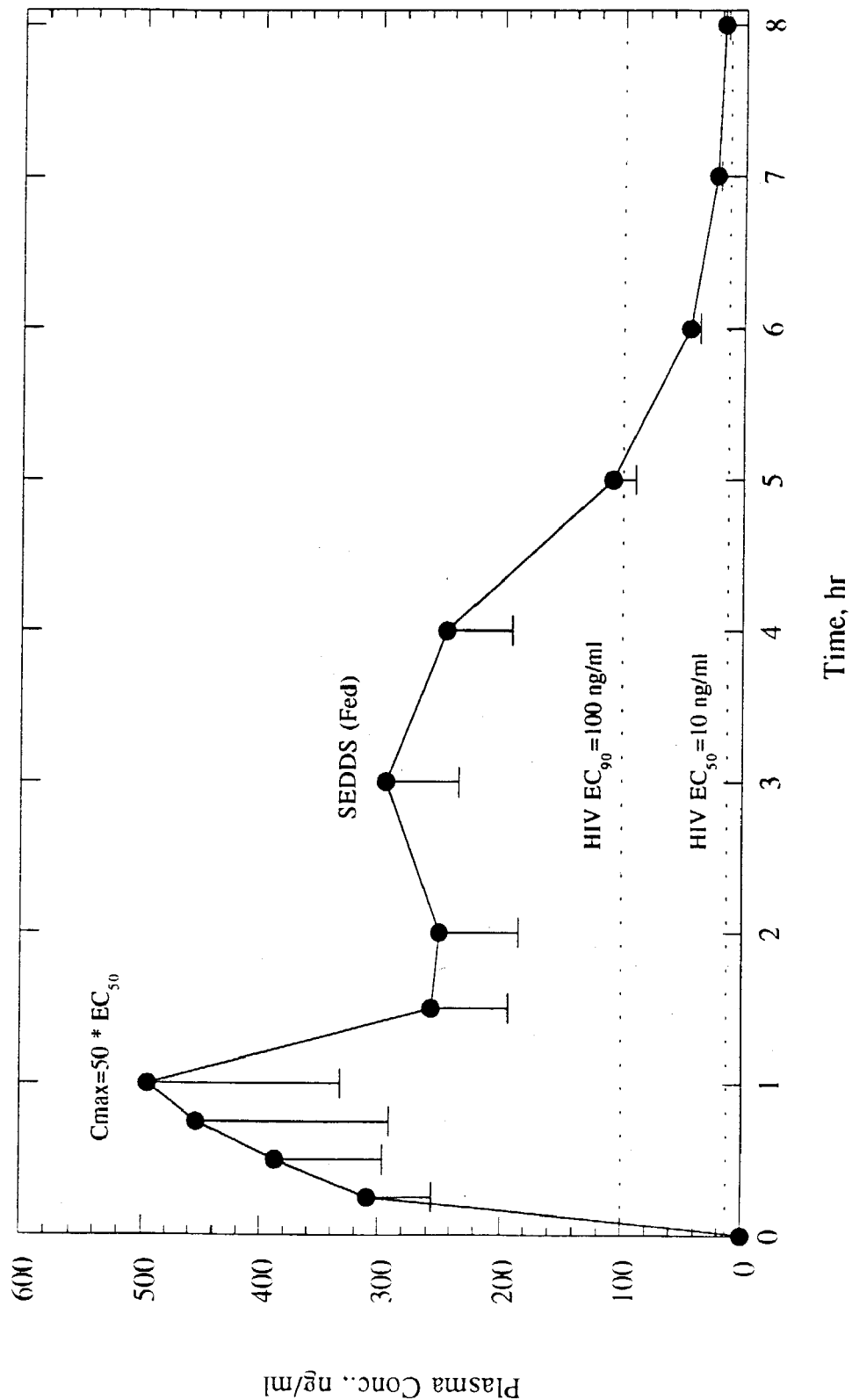
FIG. 3 shows the plasma concentration-time curve of a pharmaceutical with SEDDS fed along with the $IC_{50}$ and $IC_{90}$ pharmaceutical plasma levels.
Figure 4:
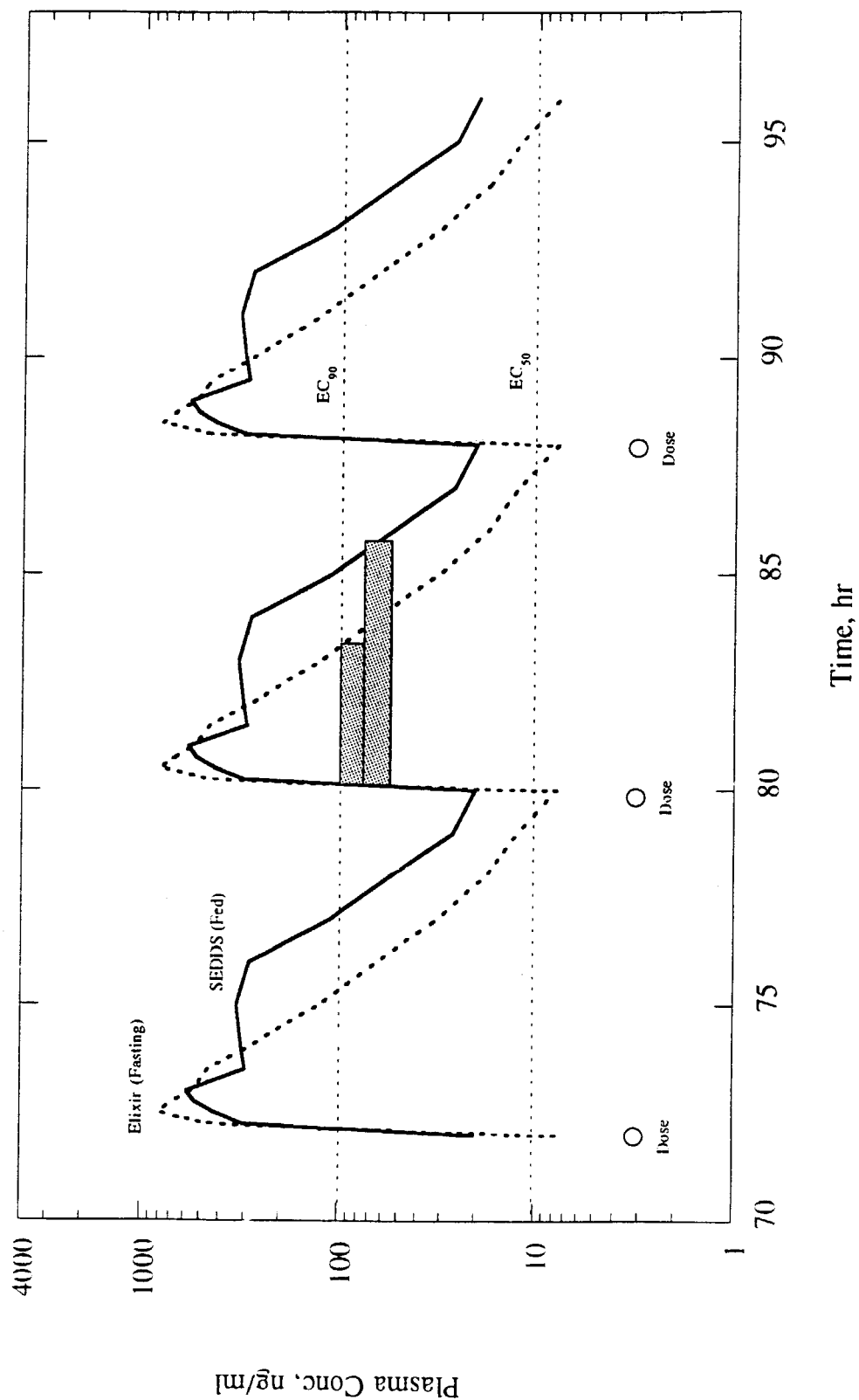
FIG. 4 shows the simulated steady state plasma concentration-time curves of a pharmaceutical with elixir fasting and SEDDS fed.

Single oral doses of $N^1$-[3-[$N^2$-[[(1,1-dimethylethyl)amino]carbonyl]-$N^2$-(2-methylpropyl)amino]-2(R)-hydroxy-1(S)-(phenylmethyl) propyl]-2(S)-[$N^3$-(2-quinolinylcarbonyl)amino]butanediamide (500 mg) were administered to human subjects as: (1) elixir (Example 6) to subjects which fasted overnight for approximately ten hours prior to each treatment (elixir fasting); (2) emulsifiable concentrate (Example 3) mixed as described above in a ratio of 1:10 in apple juice to subjects which fasted overnight for approximately ten hours prior to each treatment (SEDDS fasting); and (3) emulsifiable concentrate (Example 3) mixed as described above in a ratio of 1:10 in apple juice to subjects immediately following a high fat breakfast (SEDDS fed). Eighteen subjects (HIV positive non-symptomatic individuals) completed the three treatments in a randomized, balanced, crossover study. FIG. 1 shows the plasma concentration-time curves of the pharmaceutical with elixir fasting and SEDDS fasting. FIG. 2 shows the plasma concentration-time curves of the pharmaceutical with elixir fasting and SEDDS fed. Relative to elixir, the pharmaceutical bioavailability from SEDDS given under fasting state demonstrated no controlled release characteristics (FIG. 1). However, when SEDDS was given with food, not only was there excellent bioavailability (about 90% relative to elixir) but a highly desirable controlled release profile was obtained (FIG. 2). Mean plasma levels were almost 50 times the $IC_{50}$ (10 ng/mL) at $C_{max}$ and thereafter remained above $IC_{50}$ throughout the eight-hour projected dosing intervals. Also, mean concentrations were above $IC_{90}$ (100 ng/mL) for almost five hours after the single dose (FIG. 3). Simulated steady state plasma concentration-time curves (FIG. 4) show that compared to elixir, plasma levels with SEDDS fed remain above $IC_{90}$ for a longer time period (shaded horizontal bars).

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition in the form of an emulsion, said composition comprising an emulsified mixture of (I) an emulsifiable concentrate, comprising:
    (a) an antiviral compound that is substantially water and oil insoluble,
    (b) an edible emulsifier,
    (c) an edible oil, and
    (d) an edible solubilizer, and
(II) an aqueous solution, wherein said emulsifiable concentrate comprising (a)–(d) and said aqueous solution are present in a ratio of emulsifiable concentrate: water from about 1:10 to about 1:1000, to provide said pharmaceutical composition as an emulsion, prior to use.

2. The composition of claim 1, wherein:
    (a) said antiviral compound has a water solubility and an oil solubility of less than 1 part per hundred and has a concentration from about 0.1 to about 17% (w/w) of said emulsifiable concentrate,
    (b) said emulsifier has a concentration from about 10 to about 55% (w/w) of said emulsifiable concentrate,
    (c) said oil has a concentration from about 10 to about 50% (w/w) of said emulsifiable concentrate, and
    (d) said solubilizer has a concentration from about 2 to about 50% (w/w) of said emulsifiable concentrate.

3. The composition of claim 1, wherein said edible emulsifier is selected from the group consisting of a synthetic glycerol, a polyglycerol, sorbitol, and an ethylene glycol ester of a fatty acid; and said edible oil is selected from the group consisting of a vegetable oil, a vegetable fat, an animal oil, and an animal fat.

4. The composition of claim 1, wherein said emulsifier is selected from the group consisting of a polyoxyethylene glycerol ester of a fatty acid, an ethylene glycol ester, a propylene glycol ester, a glyceryl esters of a fatty acid, a sorbitan ester, a polyglyceryl ester, a fatty alcohol ethoxylate, an ethoxylated propoxylated block copolymer, a polyethylene glycol ester of a fatty acids, a cremophore, a glyceryl monocaprylate/caprate, and mixtures thereof; said oil is selected from the group consisting of Neobee oil, a Myglyol derivative, soy oil, almond oil, olive oil, peanut oil, a medium chain triglyceride having from about 8 to about 10 carbon atoms, and mixtures thereof and said solubilizer is selected from the group consisting of ethanol, sweet peppermint flavor, orange oil flavor, cherry flavor, raspberry flavor, lemon oil flavor, oleic acid, linoleic acid, butyric acid, propionic acid, lauryl alcohol, limenone, myristyl alcohol, and mixtures thereof.

5. The composition of claim 1, said composition further comprising a second pharmaceutical that is water soluble, oil soluble, or substantially water and oil insoluble.

6. The composition of claim 1, wherein said ratio is from about 1:50 to about 1:200.

7. The composition of claim 1, wherein said antiviral compound is an HIV protease inhibitor.

8. The composition of claim 1, wherein said aqueous solution has a pH from about 3 to about 8.5.

9. A method for preparing a pharmaceutical composition as an emulsion, said method comprising combining an emulsifiable concentrate with an aqueous solution, in a ratio of emulsifiable concentrate: water from about 1:10 to about 1:1000, to provide said pharmaceutical composition as an emulsion prior to use, wherein said emulsifiable concentrate comprises an antiviral compound that is substantially water and oil insoluble, an edible emulsifier, an edible oil, and an edible solubilizer.

10. The method of claim 9, wherein said ratio is from about 1:50 to about 1:200.

11. The method claim 9, wherein said antiviral compound is an HIV protease inhibitor.

12. The composition of claim 1, wherein said aqueous solution is water or hydrochloric acid.

13. The composition of claim 12, wherein said aqueous solution is hydrochloric acid having a concentration of about 0.1 N.

* * * * *